(12) United States Patent
Ando et al.

(10) Patent No.: US 11,464,884 B2
(45) Date of Patent: Oct. 11, 2022

(54) ANTIBACTERIAL DEVICE AND ELECTRICAL APPARATUS

(71) Applicant: Murata Manufacturing Co., Ltd., Nagaokakyo (JP)

(72) Inventors: Masamichi Ando, Nagaokakyo (JP); Kenichiro Takumi, Nagaokakyo (JP); Daiji Tamakura, Nagaokakyo (JP); Kenichi Mori, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 146 days.

(21) Appl. No.: 16/886,981

(22) Filed: May 29, 2020

(65) Prior Publication Data
US 2020/0289697 A1 Sep. 17, 2020

Related U.S. Application Data

(63) Continuation of application No. PCT/JP2019/007501, filed on Feb. 27, 2019.

(30) Foreign Application Priority Data
Mar. 5, 2018 (JP) .............................. JP2018-038226

(51) Int. Cl.
  *A61L 9/16* (2006.01)
  *A61L 2/03* (2006.01)
  *F24F 1/0076* (2019.01)
(52) U.S. Cl.
  CPC .................. *A61L 9/16* (2013.01); *A61L 2/03* (2013.01); *A61L 2209/16* (2013.01); *F24F 1/0076* (2019.02)

(58) Field of Classification Search
  CPC ................. A61L 2/03; A61L 9/16; A61L 9/22
  See application file for complete search history.

(56) References Cited

U.S. PATENT DOCUMENTS

| 2013/0064726 A1 | 3/2013 | Morfill et al. |
| 2013/0202766 A1 | 8/2013 | Rubinsky |
| 2016/0339128 A1 | 11/2016 | Fujikane et al. |

(Continued)

FOREIGN PATENT DOCUMENTS

| JP | H0762150 A | 3/1995 |
| JP | 2002010766 A | 1/2002 |

(Continued)

OTHER PUBLICATIONS

International Search Report issued for PCT/JP2019/007501, dated May 28, 2019.

(Continued)

*Primary Examiner* — Timothy C Cleveland
(74) *Attorney, Agent, or Firm* — ArentFox Schiff LLP (57) ABSTRACT

An antibacterial device that includes a substrate, a first electrode on the substrate, a second electrode on the substrate, and a protective layer covering the first electrode and the second electrode and having a first surface opposing of the substrate and a second surface opposite the first surface. Further, the first electrode and the second electrode are arranged such that the protective layer has an electric field strength on the second surface thereof of 150 kV/m or more when a voltage is applied to the first electrode or the second electrode.

10 Claims, 11 Drawing Sheets

(56) References Cited

U.S. PATENT DOCUMENTS

2017/0043154 A1    2/2017  Pelssers et al.
2019/0216291 A1*   7/2019  Koyama ............... A47L 23/205

FOREIGN PATENT DOCUMENTS

| JP | 2006222019 A | 8/2006 | | |
|---|---|---|---|---|
| JP | 2006302573 A | 11/2006 | | |
| JP | 2016215188 A | 12/2016 | | |
| JP | 2017520285 A | 7/2017 | | |
| WO | 2015008559 A1 | 1/2015 | | |
| WO | WO-2018038264 A1 * | 3/2018 | ............. | A47L 23/02 |

OTHER PUBLICATIONS

Written Opinion of the International Searching Authority issued for PCT/JP2019/007501, dated May 28, 2019.
Takaki, Koichi; "Agricultural and Food Processing Applications of High-Voltage and Plasma Technologies"; J. HTSJ, vol. 51, No. 216, Jul. 2012, pp. 64-69. (Translation of Section 5 p. 67 "Freshness retention and component exliaction by high voltage").

* cited by examiner

ANTIBACTERIAL DEVICE AND ELECTRICAL APPARATUS

CROSS REFERENCE TO RELATED APPLICATIONS

The present application is a continuation of International application No. PCT/JP2019/007501, filed Feb. 27, 2019, which claims priority to Japanese Patent Application No. 2018-038226, filed Mar. 5, 2018, the entire contents of each of which are incorporated herein by reference.

FIELD OF THE INVENTION

The present invention relates to an antibacterial device including an antibacterial function, and to an electrical apparatus including the antibacterial device.

BACKGROUND OF THE INVENTION

Conventionally, plastic products exhibiting antibacterial properties for a long period of time have been proposed (see Patent Document 1). The product described in Patent Document 1 is formed in a state in which plastic contains an antibacterial substance made of silver or silver oxide.

Patent Document 1: Japanese Patent Application Laid-Open No. H07-62150

SUMMARY OF THE INVENTION

Silver has a high antibacterial effect. Silver exerts antibacterial properties by silver ions. Normally, silver ions slightly exist on a surface of silver, but are changed to silver sulfide by sulfur dioxide gas or the like in the air. This causes an amount of silver ions existing on the surface of silver to be reduced, and therefore, the antibacterial properties are deteriorated. For this reason, in a product coated with a coating agent containing silver, the antibacterial properties decrease as the product is used for a long time. Accordingly, mold may grow as the antibacterial properties deteriorate.

Therefore, an object of the present invention is to provide an antibacterial device that exhibits antibacterial properties over a long period of time.

An antibacterial device of the present invention includes a substrate, a first electrode on the substrate, a second electrode on the substrate, and a protective layer covering the first electrode and the second electrode and having a first surface opposing the substrate and a second surface opposite the first surface. Further, the first electrode and the second electrode are arranged such that the protective layer has an electric field strength on the second surface thereof of 150 kV/m or more when a voltage is applied to the first electrode or the second electrode.

In the antibacterial device of the present invention, the electric field of 150 kV/m or more is generated on the surface (second surface) of the protective layer. The present inventors have confirmed that the antibacterial properties exist under the electric field of 150 kV/m. Therefore, the antibacterial device of the present invention can kill germs such as mold by the generated electric field.

According to the present invention, the antibacterial device that exhibits antibacterial properties over a long period of time can be realized.

DETAILED DESCRIPTION OF THE INVENTION

Figure 1:
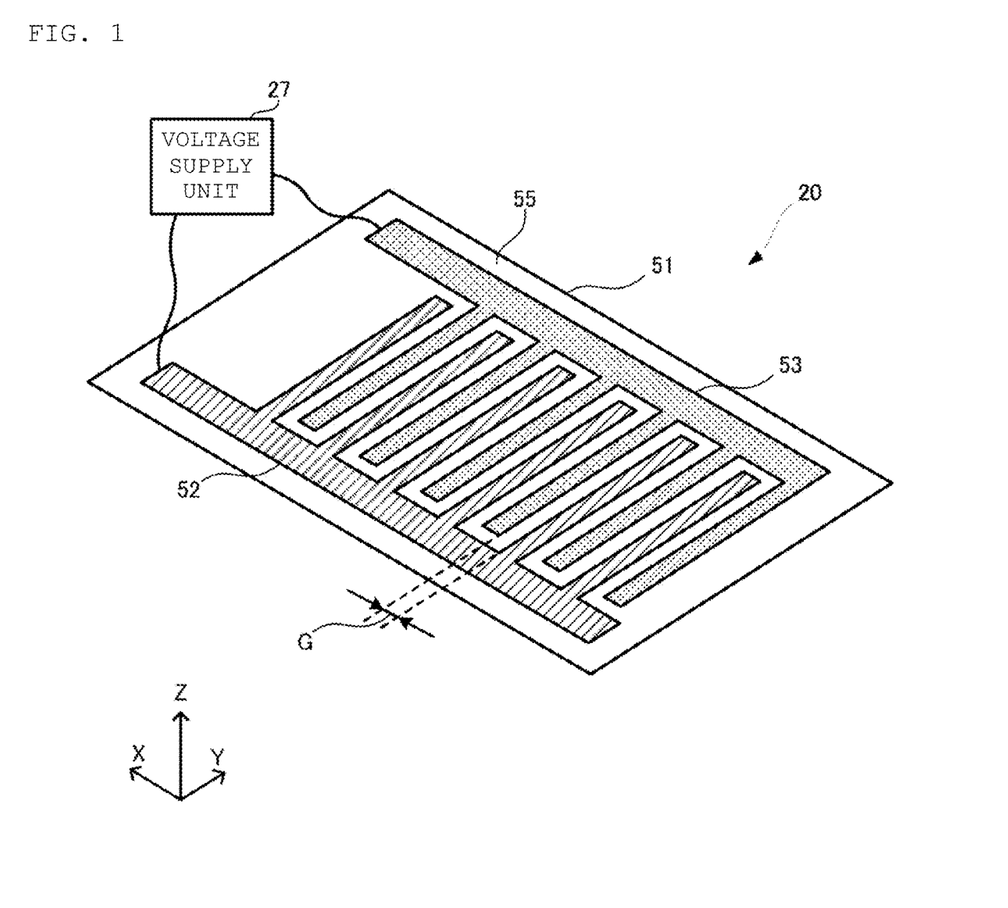
FIG. 1 is a view for explaining an antibacterial unit of an antibacterial device according to a first embodiment.

FIG. 1 is a view for explaining an antibacterial unit of an antibacterial device according to a first embodiment. As shown in FIG. 1, an antibacterial unit 20 includes a base film 51, a first electrode 52, and a second electrode 53. The first electrode 52 and the second electrode 53 are connected to a voltage supply unit 27. The voltage supply unit 27 applies a voltage to the first electrode 52 and the second electrode 53. The application of the voltage is described later in detail.

The base film 51 is an example of a substrate of the present invention. The base film 51 has a flat plate shape, and includes a first surface 55 and a second surface on a rear side of the first surface 55. The first electrode 52 and the second electrode 53 are arranged on the first surface 55 of the base film 51 in an interdigital shape. More specifically, the first electrode 52 and the second electrode 53 are each formed in a comb shape. The first electrode 52 and the second electrode 53 are arranged such that the comb teeth of both electrodes are alternately arranged with a predetermined distance G therebetween.

The base film 51 is an insulator. As the base film 51, a commonly used resin material can be used, and for example, resin material made of polyethylene terephthalate (PET), polyethylene (PE), polycarbonate (PC), acrylonitrile butadiene styrene copolymer (ABS), acryl, vinyl chloride, or the like can be exemplified.

As material of the first electrode 52 or the second electrode 53, gold (Au), silver (Ag), copper (Cu), aluminum (Al), nickel (Ni), carbon, indium tin oxide (ITO), poly(3,4- ethylenedioxythiophene) (PeDOT), MXene (Ti$_2$C) or the like can be used. Ag and Cu themselves have antibacterial properties. Similarly, MXene has strong antibacterial properties. Therefore, when Ag, Cu, or MXene is used as the material of the first electrode 52 or the second electrode 53, the first electrode 52 or the second electrode 53 exhibits even stronger antibacterial properties.

The first electrode 52 or the second electrode 53 is formed on the base film 51 by a known technique such as printing or vapor deposition. Note that the base film 51 preferably has flexibility in a state of having the first electrode 52 and the second electrode 53 arranged thereon. Thereby, a user can deform the antibacterial unit 20 according to the use situation and conform the shape to that of a place where the antibacterial unit is arranged.

Figure 8:
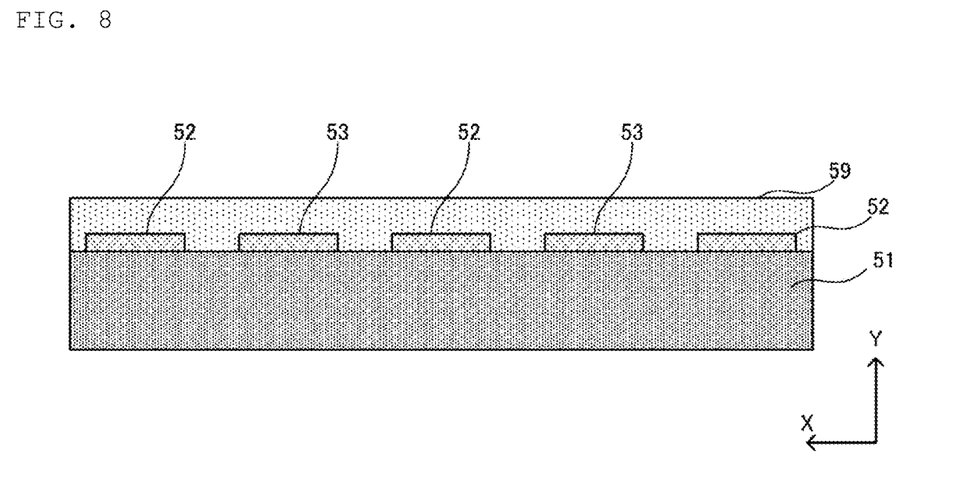
FIG. 8 is a partial cross-sectional view of an antibacterial unit 20.

The antibacterial unit 20 may further include a protective film 59 having insulating properties, as shown in FIG. 8. The protective film 59 is adhered on the base film 51 so as to cover the first electrode 52 and the second electrode 53. The protective film 59 has a first surface opposing the base film 51 and a second surface opposite to the first surface of the protective film. The second surface is exposed to the outside. Note that the protective film 59 may be formed by adhering a thin film or by coating with a thermosetting resin, a photocurable resin, or the like.

The protective film 59 prevents hydrogen from being generated by electrolysis of water by the first electrode 52 or the second electrode 53. Additionally, Ag is the material that is relatively easy to cause migration. Here, when Ag is used as the material of the first electrode 52 or the second electrode 53, the protective film 59 inhibits the migration of Ag, and accordingly, a failure of the antibacterial unit 20 can be prevented. Further, because the protective film 59 has insulating properties, safety against electric leakage, electric shock or the like due to the first electrode 52 and the second electrode 53 can be improved.

Next, application of voltage to the first electrode 52 and the second electrode 53 is described in detail. The voltage supply unit 27 applies a voltage to the first electrode 52 and the second electrode 53 in a manner that an electric field of less than 3 MV/m is generated. For example, when the distance G between the first electrode 52 and the second electrode 53 is 100 μm, the voltage supply unit 27 applies a voltage of 50 V. In this case, the electric field generated between the first electrode 52 and the second electrode 53 is 0.5 MV/m.

The breakdown strength of air is about 3 MV/m. When a voltage that generates the electric field having an electric field strength of less than 3 MV/m is applied to the first electrode 52 and the second electrode 53, the antibacterial unit 20 can stably form the electric field without causing a discharge phenomenon.

It has been known that a growth of germs can be suppressed by the presence of the electric field (e.g., refer to Koichi Takagi, Agricultural and Food Processing Applications of High-Voltage and Plasma Technologies, J. HTSJ, Vol. 51, No. 216). In addition, the germs referred to in the present embodiment include bacteria, fungi, or microorganisms such as mites or fleas.

Hereinafter, an experiment is described in which the electric field suppressing the growth of germs was confirmed.

Figure 2A:
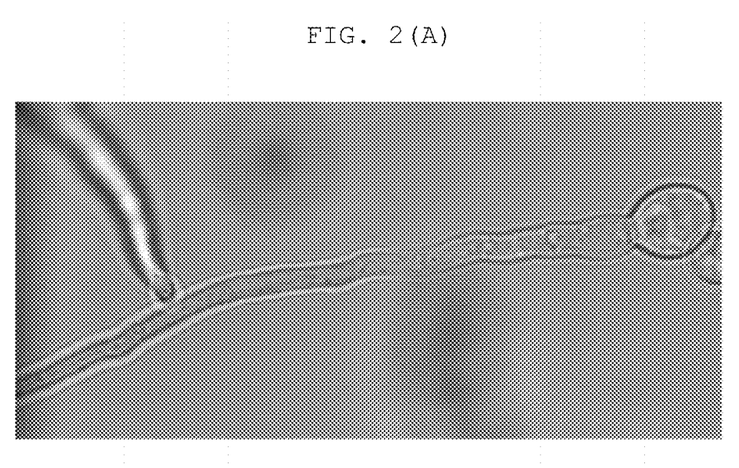
FIGS. 2(A) and 2(B) are enlarged photographs showing changes of Trichophyton in an electric field.
Figure 2B:
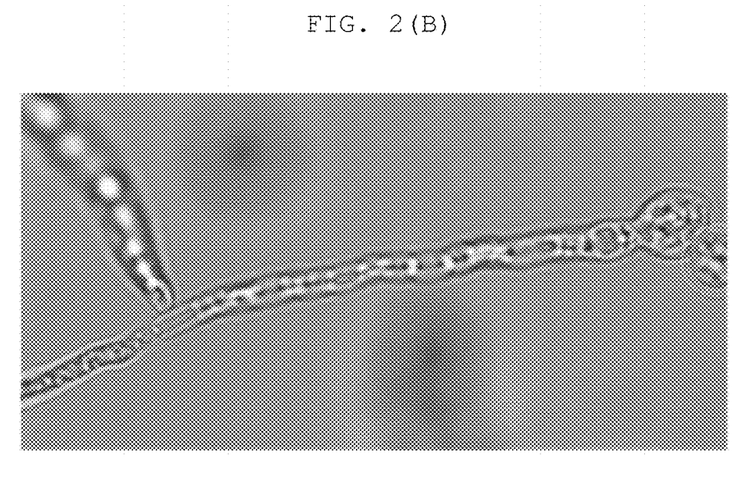

Trichophyton, a kind of mold, was used as the germs. FIGS. 2(A) and 2(B) are enlarged photographs showing changes of Trichophyton in an electric field. In this experiment, the changes of Trichophyton before and after the generation of the electric field were observed under magnification by an electron microscope.

Trichophyton in pure water was placed on a glass on which interdigital electrodes were formed. A pulse voltage of 1 MV/m, 5 Hz was applied to the interdigital electrodes for 8 seconds while Trichophyton was observed in an enlarged manner by the electron microscope. A distance between the interdigital electrodes was 100 μm, and a peak value of the applied voltage was 100 V. Trichophyton before the pulse voltage was applied and Trichophyton after the pulse voltage was applied were respectively photographed.

As shown in FIG. 2(A), it was confirmed that protoplasm was flowing in Trichophyton before the pulse voltage was applied. On the other hand, as shown in FIG. 2(B), it was confirmed that, in Trichophyton after the pulse voltage was applied, the protoplasm stopped flowing and Trichophyton stopped its activity.

This confirmed that an electric field generated by applying the pulse voltage of 1 MV/m, 5 Hz for 8 seconds stopped the activity of Trichophyton. According to the result of a moving image, the changes in a state of Trichophyton caused by the electric field occur from the moment the electric field is applied, and this implies that the pulse voltage does not need to be applied for 8 seconds. A strength of the electric field, a frequency of the pulse voltage, and an application duration are items to be determined in consideration of a type of the target germ, a habitat, and size and interval of the interdigital electrodes. As in this case, when the pulse voltage of 5 Hz for 8 seconds was applied, a sufficient antibacterial effect was obtained even when the electric field strength was 1 MV/m. The same experiment was performed with the applied voltage further reduced, and it was confirmed that protoplasm stopped flowing when the pulse voltage of 30 V was applied, that is, even when the electric field strength was 0.3 MV/m. As a result, it was confirmed that the inhabiting germs were killed by applying an electric field pulse having the electric field strength of less than 3 MV/m. This means that it was confirmed that the growth of germs could be suppressed. In addition, because Trichophyton cells are once destroyed, the growth of mold can be sufficiently suppressed by intermittently applying the voltage for several seconds in consideration of a growth rate of mold. For example, there is a case in which the pulse voltage of 1 MV/m, 5 Hz is applied once every 24 hours for several seconds.

The antibacterial unit 20 can exert an antibacterial effect by an electric field formed near the antibacterial unit 20. The voltage applied to the first electrode 52 and the second electrode 53 is preferably applied such that the electric field between the first electrode 52 and the second electrode 53 becomes 0.3 MV/m or more, more preferably 1 MV/m. If the electric field is 0.3 MV/m or more, the antibacterial unit 20 can sufficiently exhibit the antibacterial effect.

For example, when the distance G between the first electrode 52 and the second electrode 53 is 100 μm and the applied voltage is 100 V, the generated electric field is 1 MV/m. When the distance G between the first electrode 52 and the second electrode 53 is 50 μm, the voltage applied to generate the electric field of 1 MV/m is 50 V. As described above, the smaller the distance G between the first electrode 52 and the second electrode 53, the lower the applied voltage, and thus the higher the safety.

Further, the voltage supply unit 27 applies the voltage such that the average electric field strength on the upper surface (second surface) of the protective film 59 becomes 150 kV/m or more.

Figure 9A:
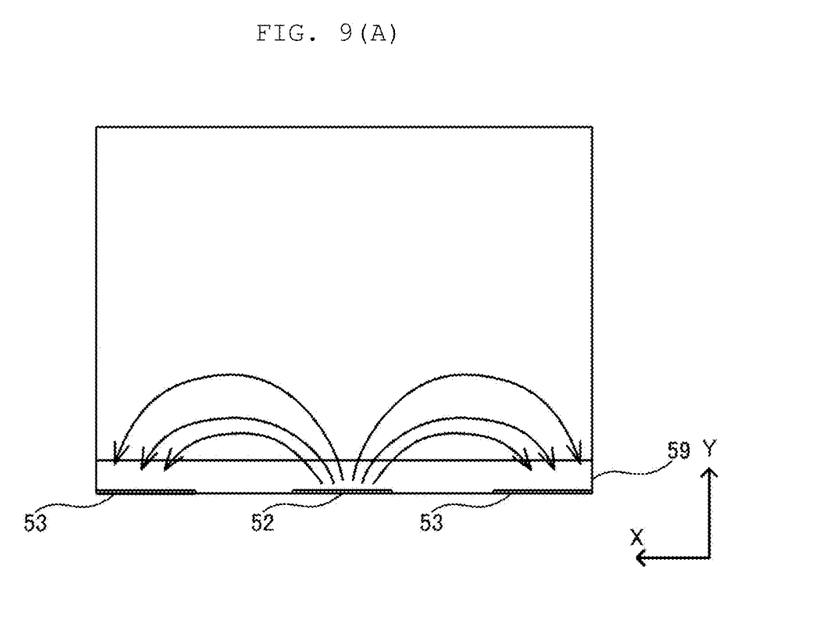
FIG. 9(A) is a view showing electric field vectors generated on a second surface of a protective film 59 when a voltage of 100 V is applied to a first electrode 52.
Figure 9B:
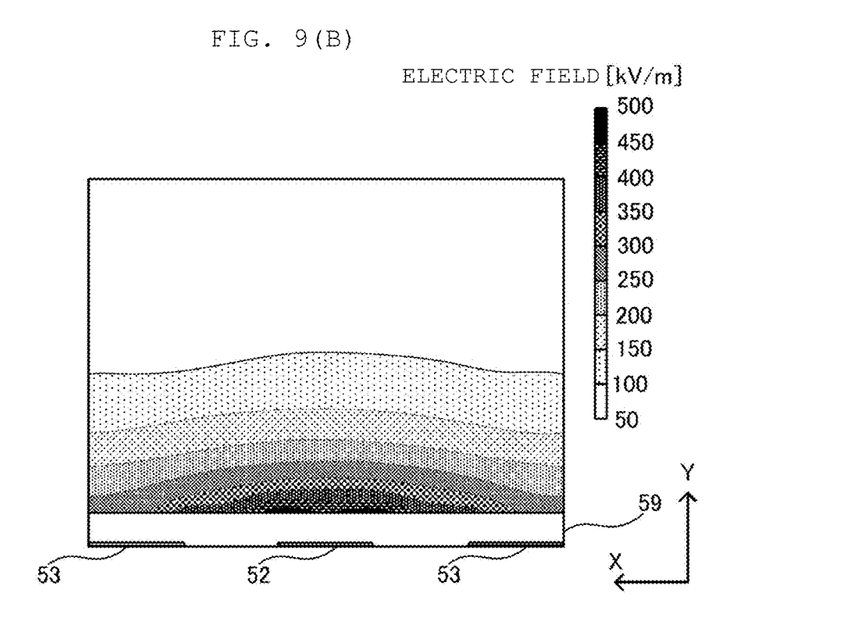
FIG. 9(B) is a view showing an electric field strength.

FIG. 9(A) is a diagram showing electric field vectors generated on the second surface of the protective film 59 when a voltage of 100 V is applied to the first electrode 52. FIG. 9(B) is a diagram showing the electric field strength.

As shown in FIG. 9(A), a fringe-like electric field is generated on the second surface of the protective film 59, and an electric field is generated from the second surface to the upper portion thereof. As shown in FIG. 9(B), the electric field of about 450 kV/m is generated on the second surface where the electric field is the strongest. Further, the electric field of about 150 kV/m is generated even at a position (for example, 30 μm) separated to some extent from the second surface of the protective film 59.

Figure 10:
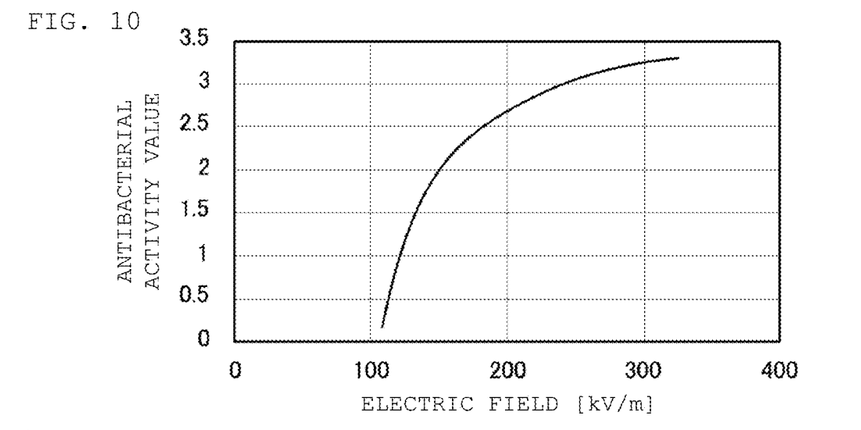
FIG. 10 is a graph showing a relationship between an average electric field strength generated on the second surface and an antibacterial activity value to mold fungi (*Aspergillus niger*).

FIG. 10 is a graph showing a relationship between the average electric field strength generated on the second surface and an antibacterial activity value to mold fungi (*Aspergillus niger*). The antibacterial activity value was measured under the following conditions.

Antibacterial activity value: $A=(Mb-Ma)-(Mc-Mo)$

Ma: Arithmetic mean common logarithm of a viable bacterial count (or amount of ATP) of a reference (device to which no voltage is applied) immediately after inoculation of test germs Mb: Arithmetic mean common logarithm of the viable bacterial count (or amount of ATP) of the reference after culturing for 42 hours Mo: Arithmetic mean common logarithm of the viable bacterial count (or amount of ATP) of the antibacterial device immediately after inoculation of test germs Mc: Arithmetic mean common logarithm of the viable bacterial count (or amount of ATP) of the antibacterial device after culturing for 42 hours The culturing duration of mold fungi was 42 hours, and the culturing temperature was 25° C. Normal antibacterial products have an antibacterial activity value $A \geq 2.0$.

As shown in the results shown in FIG. 10, when the voltage is applied such that the average electric field strength becomes 150 kV/m or more, the antibacterial activity value A becomes 2.0 or more, and it can be confirmed that a sufficient antibacterial effect is obtained. Note that the voltage applied to the first electrode 52 and the second electrode 53 may be a standing wave, pulse wave, or alternating voltage. For example, when the voltage applied to the first electrode 52 and the second electrode 53 is alternating, the frequency may be 1 Hz to 10 Hz. In addition, a duration of several seconds is sufficient for applying the voltage to the first electrode 52 and the second electrode 53. The respective conditions such as the duration for applying voltage can be set in consideration of the environment in which the antibacterial unit 20 is arranged, the season, and the type of mold that tends to grow.

The voltage applied to the first electrode 52 and the second electrode 53 does not need to be applied frequently, and may be applied at a timing that inhibits the generation or growth of mold. For example, the frequency of applying the voltage may be three times a day, that is, every eight hours. The user can set the frequency according to a condition of mold generation. As described above, because the applied voltage may be intermittent, the power consumption is significantly reduced as compared with the case in which the voltage is continuously applied.

Figure 3:
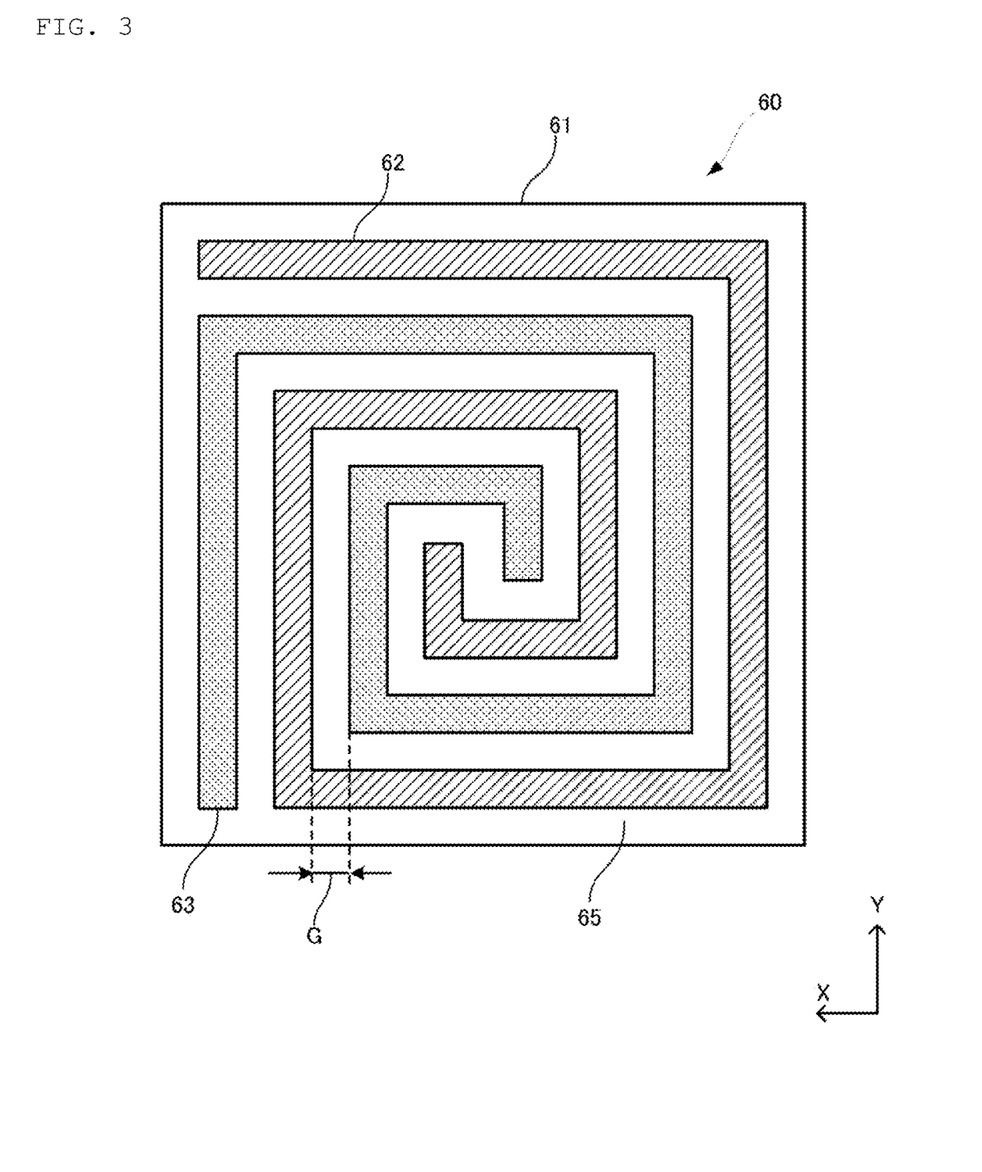
FIG. 3 is a plan view for explaining an antibacterial unit according to a modified example of the first embodiment.

FIG. 3 is a plan view for explaining an antibacterial unit according to a modified example of the first embodiment. An antibacterial unit 60 according to the modified example has the same structure as the antibacterial unit 20 except that shapes of a first electrode and a second electrode are different from those of the antibacterial unit 20. For this reason, in the description of the antibacterial unit 60, the description of the same configuration as the antibacterial unit 20 is omitted, and only the shapes of the electrodes are described.

As shown in FIG. 3, the antibacterial unit 60 includes a first electrode 62 and a second electrode 63 on a first surface 65 of a base film 61. Each of the first electrode 62 and the second electrode 63 has a spiral shape. The first electrode 62 and the second electrode 63 are arranged such that both electrodes are alternately arranged with a predetermined distance G therebetween. When a voltage is applied to the first electrode 62 and the second electrode 63, an electric field is generated between the first electrode 62 and the second electrode 63. Thereby, the antibacterial unit 60 can sufficiently exhibit the antibacterial effect similarly to the antibacterial unit 20.

Figure 4:
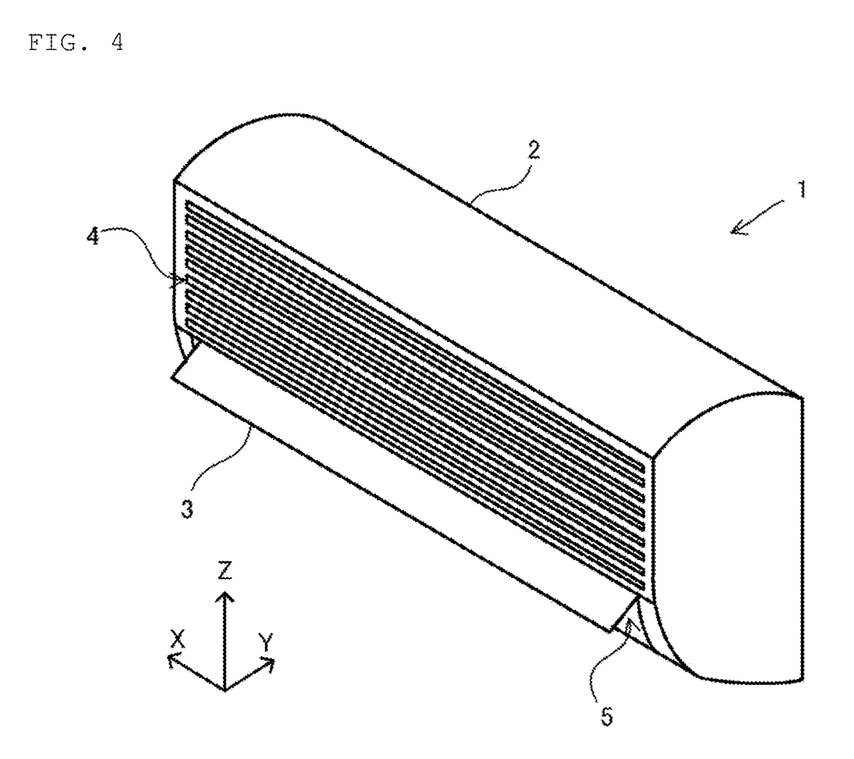
FIG. 4 is a view for explaining an electrical apparatus according to the first embodiment.
Figure 5A:
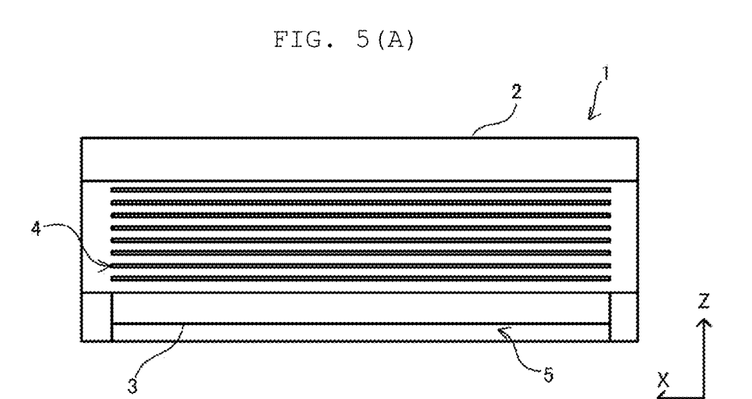
FIG. 5(A) is a front view of the electrical apparatus according to the first embodiment.
Figure 5B:
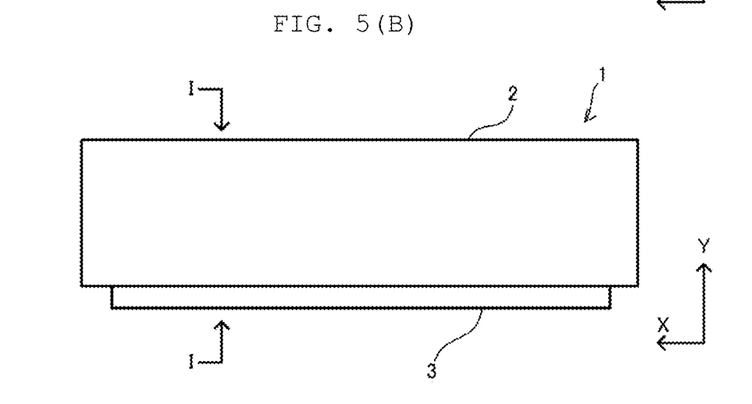
FIG. 5(B) is a plan view thereof.
Figure 5C:
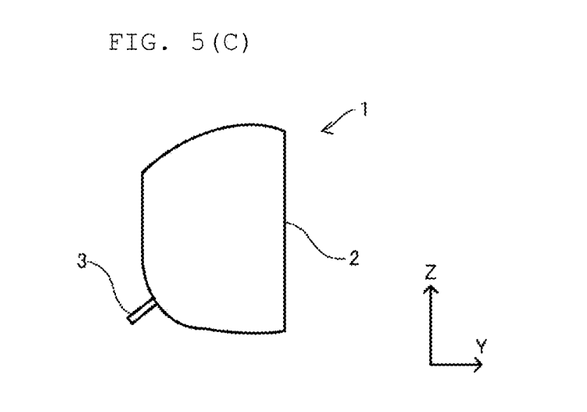
FIG. 5(C) is a side view thereof.

FIG. 4 is a view for explaining an electrical apparatus according to the first embodiment. FIG. 5(A) is a front view of the electrical apparatus according to the first embodiment, and FIG. 5(B) is a plan view thereof, and FIG. 5(C) is a side view thereof. For convenience of description, each drawing shows a state in which the electrical apparatus according to the first embodiment is in use.

As shown in FIGS. 4, 5(A), 5(B), and 5(C), an air conditioner 1 includes a housing 2, a cover 3, an air inlet 4, and an air outlet 5. The air conditioner 1 is an example of the "electrical apparatus" according to the present invention.

The cover 3, the air inlet 4, and the air outlet 5 are arranged on a front surface of the air conditioner 1. The cover 3 allows the air outlet 5 to be opened and closed.

Figure 6A:
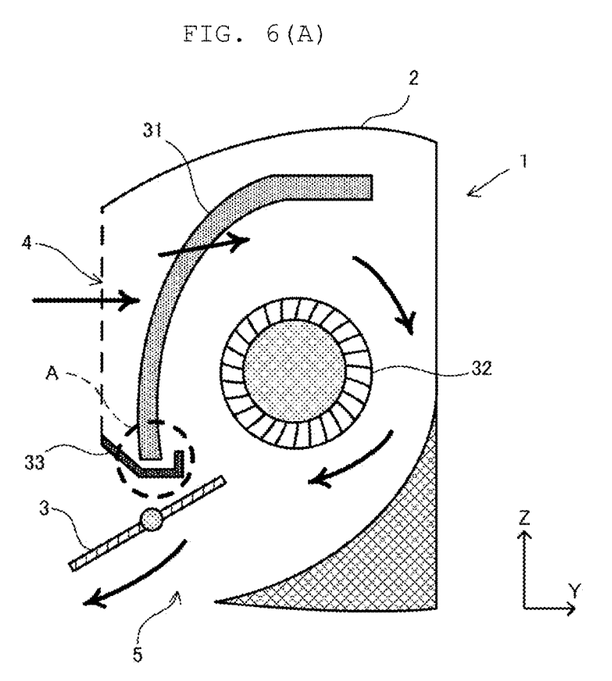
FIG. 6(A) is a schematic cross-sectional view of FIG. 5(B)
Figure 6B:
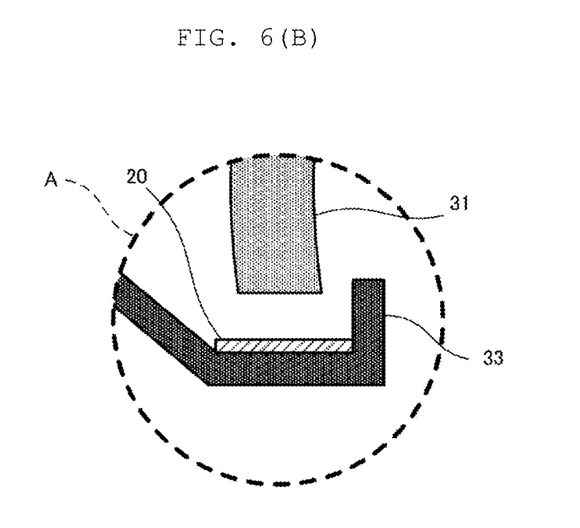
FIG. 6(B) is an enlarged view of a region A shown in FIG. 6(A).

FIG. 6(A) is a schematic cross-sectional view of the electrical apparatus according to the first embodiment shown in FIG. 5(B) cut along a line I-I, and FIG. 6(B) is an enlarged view of a region A shown in FIG. 6(A). FIGS. 6(A) and 6(B) show only necessary parts for convenience of description, and the other parts are omitted. For example, a thickness of the housing 2 is omitted and shown only by lines. In FIG. 6(A), a flow of gas is indicated by thick arrows.

As shown in FIG. 6(A), the air conditioner 1 includes a heat exchanger 31, a fan 32, and a drain pan 33 inside. The heat exchanger 31 is formed so as to surround at least a part of the periphery of the fan 32. In the present embodiment, the heat exchanger 31 is formed on the front side of the air conditioner 1, but may be arranged on the rear side. The drain pan 33 is located below the heat exchanger 31.

When a cooling function is used in the air conditioner 1, the indoor air is taken into the air conditioner 1 from the air inlet 4. The intake air is cooled by the heat exchanger 31. On the surface of the heat exchanger 31, the moisture in the air cools and condenses. Because the drain pan 33 is located below the heat exchanger 31, the drain pan 33 can serve as a tray for receiving water condensed in the heat exchanger 31. The water collected in the drain pan 33 may be discharged to the outside of the air conditioner 1 through a drain hose (not shown) or the like. The air cooled by the fan 32 is blown out to the outside of the air conditioner 1 through the air outlet 5. The drain pan 33 is often wet with water during use of the air conditioner 1, and dries after use. The environment as such generates an environment in which mold easily grows on the drain pan 33 itself or around the drain pan 33.

As shown in FIG. 6(B), the antibacterial unit 20 is arranged on the drain pan 33 on a side of the heat exchanger 31. FIG. 6(B) shows an example in which the antibacterial unit 20 is installed in the drain pan 33. The antibacterial unit 20 generates an electric field on the drain pan 33. An antibacterial action is exerted by the electric field generated by the antibacterial unit 20.

Therefore, the antibacterial unit 20 prevents the generation of mold on the drain pan 33 by the generated electric field. The antibacterial unit 20 can prevent germs or microorganisms from propagating due to water attached inside the drain pan 33. For this reason, it is possible to suppress the occurrence of mold or the like in the drain pan 33 arranged inside the air conditioner 1 which is difficult for the user to maintain. Note that it is not always necessary to install the antibacterial unit 20 in the drain pan 33. For example, the antibacterial unit 20 can be installed in any location where mold is likely to occur without impairing the function of the air conditioner 1, and can be attached in consideration of characteristics of shapes of respective models of the air conditioners.

Note that, in the air conditioner 1 according to the present embodiment, the voltage supply unit 27 can use a power supply and a function included in the air conditioner 1 itself. For example, the user may set the frequency of applying the voltage to the antibacterial unit 20 in an operating device for setting the temperature of the air conditioner 1.

Figure 7A:
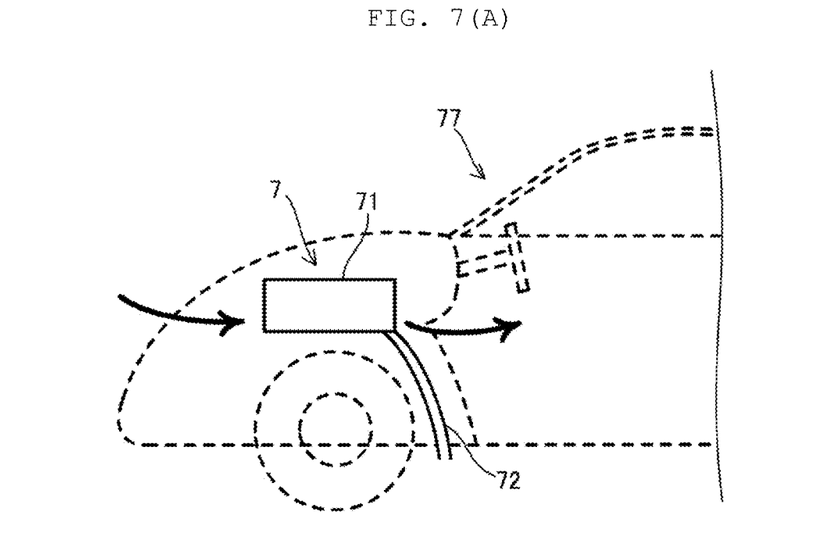
FIG. 7(A) is a view illustrating an electrical apparatus according to a second embodiment.
Figure 7B:
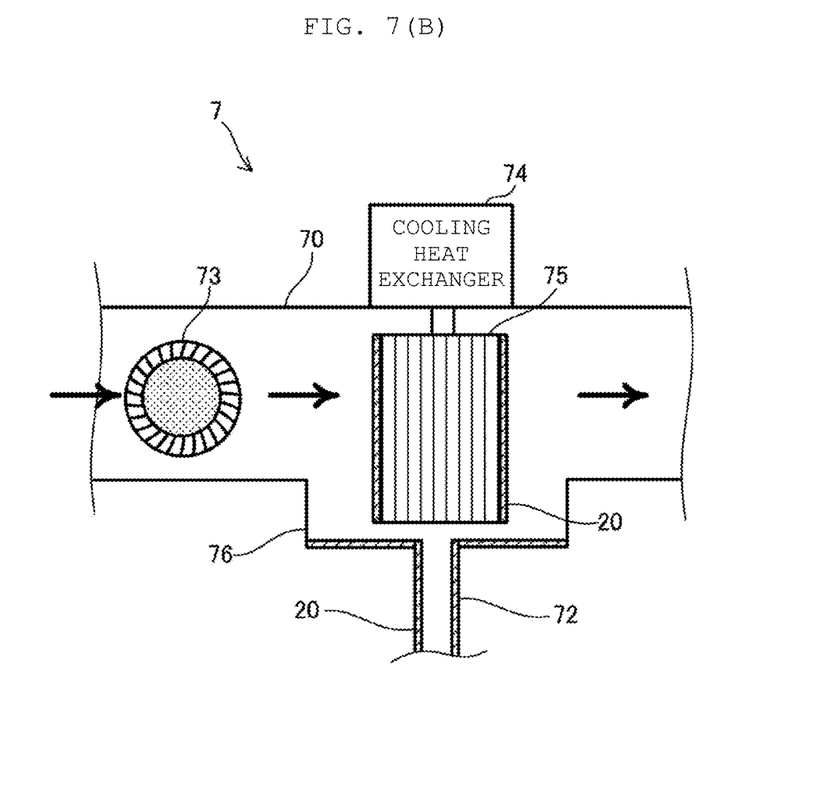
FIG. 7(B) is a partially enlarged schematic view of the electrical apparatus shown in FIG. 7(A).

FIG. 7(A) is a view for explaining an electrical apparatus according to a second embodiment. FIG. 7(B) is a partially enlarged schematic view of the electrical apparatus shown in FIG. 7(A). FIGS. 7(A) and 7(B) show a part of the electrical apparatus according to the second embodiment as cross-sectional views for convenience of description. In FIGS. 7(A) and 7(B), a flow of gas is indicated by thick arrows.

As shown in FIG. 7(A), an air conditioner 7 according to the second embodiment is mounted inside a vehicle 77 shown by a broken line. The air conditioner 7 is an example of the "electrical apparatus" according to the present invention. In a description of the air conditioner 7, the description of the same configuration as the air conditioner 1 is omitted.

The air conditioner 7 includes an air conditioner main body 71 and a drain hose 72. The drain hose 72 is drawn out of the vehicle 77 from the air conditioner main body 71 and is a hose for discharging water generated in the air conditioner main body 71 to the outside.

As shown in FIG. 7(B), the air conditioner 7 includes a duct 70, the drain hose 72, a fan 73, a cooling heat exchanger 74, an evaporator 75, a drain pan 76, and the antibacterial unit 20. The fan 73 and the evaporator 75 are arranged inside the duct 70. The fan 73 is arranged on the air inlet side (not shown) of the air conditioner 7, but may be any one that generates a predetermined gas flow inside the duct 70, and may be arranged on the air outlet side (not shown).

The cooling heat exchanger 74 is connected to the evaporator 75. The cooling heat exchanger 74 cools the evaporator 75. The drain pan 76 is located below the evaporator 75. The drain hose 72 is arranged so as to be drawn out of the air conditioner 7 from below the drain pan 76.

The antibacterial unit 20 is arranged on the evaporator 75, the drain pan 76, or the drain hose 72. The evaporator 75 cooled by the cooling heat exchanger 74 cools the gas flowing inside the duct 70. The water contained in the gas inside the duct 70 condenses on a surface of the evaporator 75. The drain pan 76 receives the condensed water, and the water collected in the drain pan 76 is discharged to the outside of the duct 70 through the drain hose 72 and then discharged to the outside of the vehicle 77.

The antibacterial unit 20 is arranged at a location where moisture is generated in the air conditioner 7. The antibacterial unit 20 exerts the antibacterial action by the electric field generated by the antibacterial unit 20. Therefore, the antibacterial unit 20 can impart the antibacterial action to the evaporator 75, the drain pan 76, or the drain hose 72. Therefore, the antibacterial unit 20 can suppress the generation of mold and the like even in the air conditioner 7 mounted inside the vehicle 77 which is usually difficult for the user to maintain.

In the present embodiment, the air conditioner as the indoor air conditioner 1 and the vehicle-mounted air conditioner 7 have been described as the examples of the electrical apparatuses, however, the present invention is not necessarily limited thereto. The electrical apparatus includes an apparatus that generates moisture. The electrical apparatus includes, for example, a microwave oven, a refrigerator, a rice cooker, a juicer, a vacuum cleaner, a washing machine, an electric pot, a humidifier, an automatic faucet, a toilet, and an electrical apparatus used around the bathroom. In addition, the electrical apparatus includes a medical instrument such as an infusion pump, a dialysate supply device, a blood component sampling device, and a respirator, a health care product such as an electric toothbrush and a sterilization device for contact lenses, an experimental devices such as a shaker, a clean bench, an autoclave, and an incubator, or a large installation such as a hydroponics unit in a plant factory, a processing apparatus in a food processing factory, a belt conveyor, and a packing device.

In the present embodiment, the size or shape of the antibacterial unit, the number or size of the electrodes, and the like are design items that can be arbitrarily determined according to the electrical apparatus in which the antibacterial unit is installed.

Figure 11:
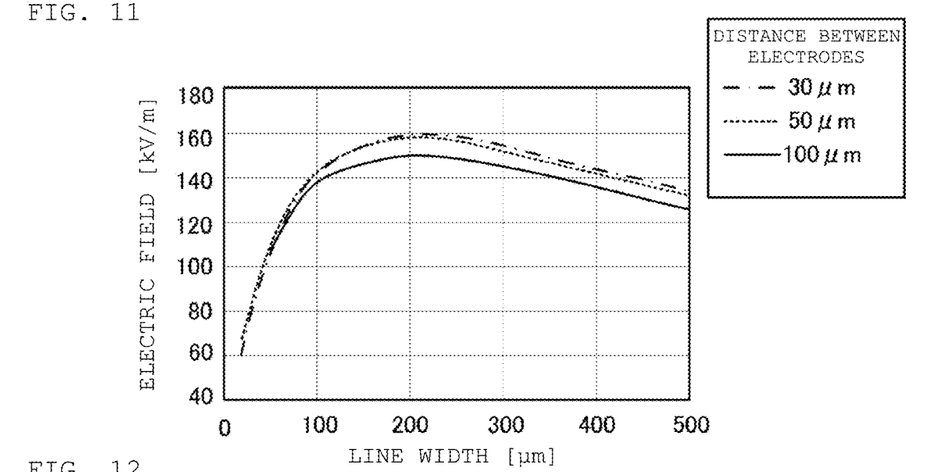
FIG. 11 is a graph showing a relationship between a width of an electrode and the average electric field strength.

FIG. 11 is a graph showing a relationship between a width of the electrode and the average electric field strength. As shown in FIG. 11, regardless of the distance between the electrodes, when the width of the electrode becomes smaller than 100 μm, the average electric field strength is significantly reduced. Therefore, when the width of the electrode is smaller than 100 μm, a high voltage is required to obtain a desired electric field. On the other hand, when the width of the electrode is 100 μm or more, a sufficient electric field can be obtained. Therefore, it is not necessary to apply an excessively high voltage. That is, when the width of the electrode is 100 μm or more, the antibacterial device that can be driven even at a low voltage can be realized.

Figure 12:
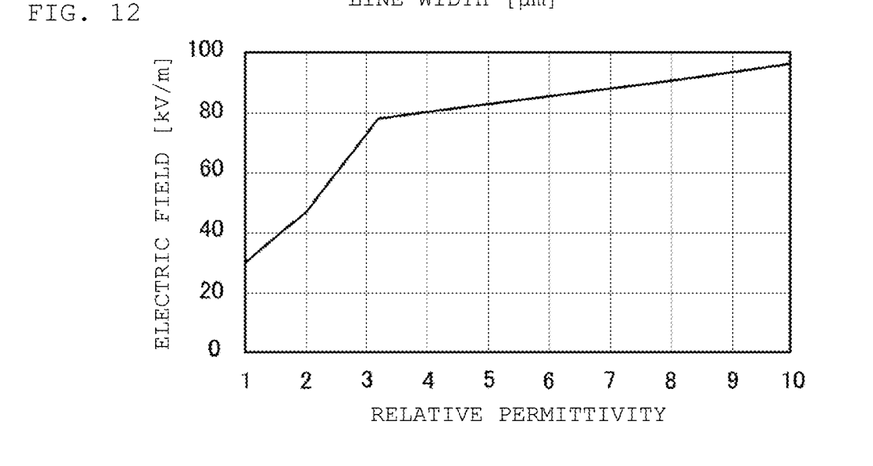
FIG. 12 is a graph showing a relationship between a relative permittivity of the protective film 59 and the average electric field strength.

FIG. 12 is a graph showing a relationship between a relative permittivity of the protective film 59 and the average electric field strength. As shown in FIG. 12, when the relative permittivity of the protective film 59 is less than 3, the average electric field strength is significantly reduced. Therefore, when the relative permittivity is less than 3, a high voltage is required to obtain a desired electric field. On the other hand, when the relative permittivity is 3 or more, a sufficient electric field can be obtained. Therefore, it is not necessary to apply an excessively high voltage. That is, when the relative permittivity is 3 or more, the antibacterial device that can be driven even at a low voltage can be realized.

Figure 13A:
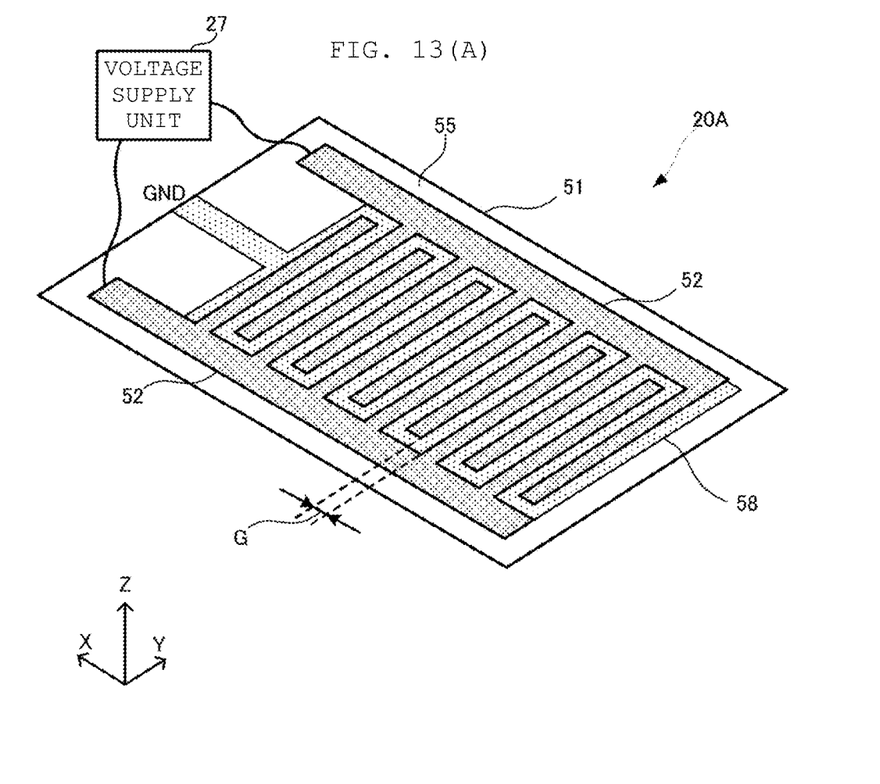
FIG. 13(A) is a perspective view showing an antibacterial unit 20A according to a modified example of the first embodiment.
Figure 13B:
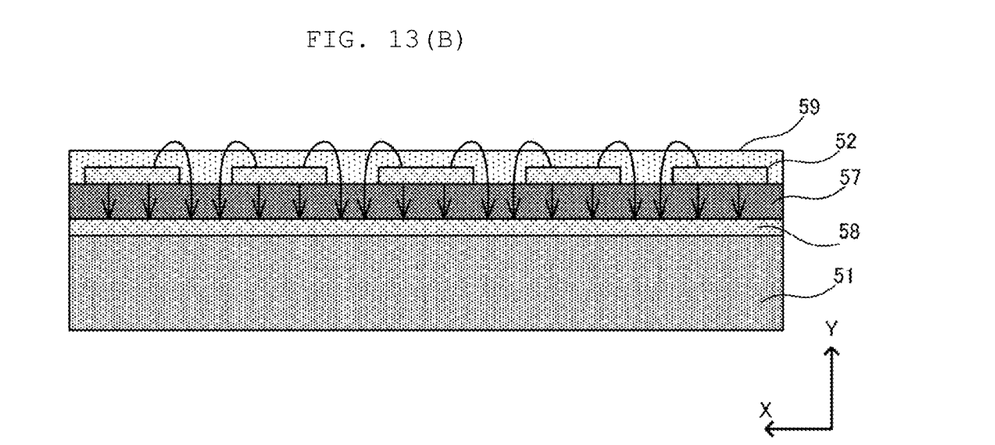
FIG. 13(B) is a partial cross-sectional view of the antibacterial unit 20A.

Next, FIG. 13(A) is a perspective view showing an antibacterial unit 20A according to a modified example of the first embodiment. FIG. 13(B) is a partial cross-sectional view of the antibacterial unit 20A. In FIG. 13(A), the same components as those in FIG. 1(A) are denoted by the same reference numerals, and the description thereof is omitted. Also, in FIG. 13(B), the same components as those in FIG. 8 are denoted by the same reference numerals, and the description thereof is omitted.

The antibacterial unit 20A includes a plurality of first electrodes 52, a second electrode 58, and an insulating layer 57. The second electrode 58 is formed on the first surface of the base film 51. The second electrode 58 is an electrode having a flat plate shape, and has an area that covers the plurality of first electrodes 52 in a plan view.

The insulating layer 57 is formed on the first surface of the base film 51 so as to cover the second electrode 58. The insulating layer 57 has a first surface arranged on a side of the base film 51 and a second surface arranged on the opposite side to the base film 51. The insulating layer 57 may be made of the same material as the base film 51, or may be made of different material. For the insulating layer 57, for example, resin material such as polyethylene terephthalate (PET), polyethylene (PE), polycarbonate (PC), acrylonitrile butadiene styrene copolymer (ABS), acryl, vinyl chloride, or the like can be exemplified.

The plurality of first electrodes 52 is formed on the second surface of the insulating layer 57. The plurality of first electrodes 52 is arranged in an interdigital shape.

The protective film 59 is adhered on the second surface of the insulating layer 57 so as to cover the plurality of first electrodes 52. An upper surface of the protective film 59 is exposed to the outside.

The second electrode 58 having the flat plate shape has, for example, a ground potential. The same voltage (for example, 100 V) is applied to all of the plurality of first electrodes 52. Thus, an electric field is formed between the plurality of first electrodes 52 and the second electrode 58. The electric field is generated not only inside the insulating layer 57 but also on the second surface of the protective film 59. On the second surface of the protective film 59, a fringe-shaped electric field is generated. Therefore, an electric field is generated even at a position distant to some extent from the second surface of the protective film 59.

In this modified example, the plurality of first electrodes 52 to which a voltage is applied and the second electrode 58 at the ground potential are not arranged on the same plane. The electrodes arranged in the interdigital shape are all at the same potential. Therefore, even if the electrodes arranged in the interdigital shape come into contact with each other, a large current does not flow, and the safer antibacterial device can be realized.

Finally, the description of the present embodiment is illustrative in all aspects and should not be construed as limiting. The scope of the present invention is defined by the terms of the claims, rather than the embodiments described above. Furthermore, it is intended that the scope of the present invention includes all modifications within the meaning equivalent to the scope of the claims and within the scope.

DESCRIPTION OF REFERENCE SYMBOLS

1, 7: Air conditioner (Electrical apparatus)
20: Antibacterial device
51: Base film (Insulator)
52, 62: First electrode
53, 63: Second electrode
55: First surface

The invention claimed is:

1. An antibacterial device comprising:
   a substrate;
   a first electrode on the substrate;
   a second electrode on the substrate;
   a protective layer covering the first electrode and the second electrode, the protective layer having a first surface opposing the substrate and a second surface opposite the first surface; and
   a voltage supply unit constructed to intermittently apply a voltage to the first electrode and the second electrode such that the protective layer produces an electric field having an electric field strength on the second surface thereof of 150 kV/m or more without causing a discharge phenomenon.

2. The antibacterial device according to claim 1, wherein the first electrode and the second electrode are arranged in an interdigital shape.

3. The antibacterial device according to claim 1, wherein the first electrode and the second electrode are arranged in a spiral shape.

4. The antibacterial device according to claim 1, wherein each of the first electrode and the second electrode has a width of 100 µm or more.

5. The antibacterial device according to claim 1, wherein the protective layer has a relative permittivity of 3 or more.

6. The antibacterial device according to claim 1, wherein the voltage is a pulse wave.

7. The antibacterial device according to claim 1, wherein the protective layer has a film shape.

8. The antibacterial device according to claim 1, wherein the protective layer is constructed to prevent hydrogen from being generated by electrolysis of water by the first electrode or the second electrode.

9. The antibacterial device according to claim 1, wherein the first electrode and the second electrode are on a same surface of the substrate.

10. An electrical apparatus comprising the antibacterial device according to claim 1.

* * * * *